United States Patent [19]

Sutter

[11] Patent Number: 4,651,145

[45] Date of Patent: Mar. 17, 1987

[54] COMMUNICATION SYSTEM FOR THE DISABLED IN WHICH A DISPLAY TARGET IS SELECTED BY ENCEPHALOGRAM RESPONSE

[75] Inventor: Erich E. Sutter, Redwood City, Calif.

[73] Assignee: Medical Research Institute, San Francisco, Calif.

[21] Appl. No.: 615,962

[22] Filed: May 31, 1984

[51] Int. Cl.$^4$ ............................................. G09G 3/00
[52] U.S. Cl. ................................... 340/706; 340/712; 340/825.19
[58] Field of Search ................... 340/825.19, 706, 712, 340/700, 705, 707

[56] References Cited

U.S. PATENT DOCUMENTS 4,158,196 6/1979 Crawford, Jr. ............... 340/825.19
4,293,855 10/1981 Perkins ......................... 340/825.19

OTHER PUBLICATIONS

*Eye-Opening Body Language;* Smart, Washington Post, p. B5, 9/17/86.

Primary Examiner—Marshall M. Curtis
Attorney, Agent, or Firm—Flehr, Hohbach, Test, Albritton & Herbert

[57] ABSTRACT

A method of oculo-encephalographic communication in which a plurality of optical stimuli provide unique code which can be identified from the EEG of viewer. The code is preferably an M-sequence binary code whereby simultaneous testing can be employed to identify the viewed optical stimulus.

A special binary sequence, or M-sequence, is utilized from which a viewed element be identified through use of a response template or sample response as predetermined from the user's encephalogram.

8 Claims, 2 Drawing Figures

FIG.—1

COMMUNICATION SYSTEM FOR THE DISABLED IN WHICH A DISPLAY TARGET IS SELECTED BY ENCEPHALOGRAM RESPONSE

This invention relates generally to gaze controlled communication systems, and more particularly the invention relates to an oculo-encephalographic communication system using a matrix of visual stimuli which can be identified from a user's encephalogram (EEG).

A sizable segment of the handicapped population is non-vocal and has no adequate motor output for communication by means of hand or foot switches or head pointers. There is at the present time no adequate communication device commercially available to cover this need. Since most persons in this category have adequate vision and oculo motor control, it has been suggested that eye movements might be an effective output channel. See for example Rosen et al, "A Display Board for Non-Vocal Communication Encoded as Eye Movements", Proceedings of the Conference on Systems and Devices for the Disabled, 1976, pgs. 70-71. The more sophisticated designs among these systems have great potential in regards to speed and efficiency, since they permit random access to a two dimensional array of selectable elements which gaze control communication an attractive solution even in cases where operation of a single switch is impossible. Gaze systems which operate on the basis of combined tracking of eye and head position are described by Foulds et al, "A Computerized Line of Gaze System For Rapid Non-Vocal Communication", National Computer Conference, 1979, and Friedman et al, "Eye Tracker Communication System", Proceedings Fifth Annual Conference on Rehabilitation Engineering, 1982, pg. 27.

The present invention overcomes the difficult tracking problem associated with such line of gaze systems and obviates the need for expensive and delicate equipment for tracking of eye and head position. Briefly, a plurality of optical stimuli such as a visual matrix or keyboard is provided which produces a unique evoked response on the scalp of the user depending on the element he fixates. This element can thus be identified through analysis of the EEG signal derived from the back of the head by conventional EEG electrodes. The feasibility of the approach is based on the following simple fact of visual anatomy and physiology. A stimulus covering the central one degree of one's visual field stimulates a much larger area of the visual cortex of the brain than the same stimulus placed in a more peripheral location. Among a large number of equivalent stimuli within one's visual field, the stimulus which is directly viewed produces a disproportionately large scalp signal. Thus, the matrix elements must be appropriately modulated in time to make identification of the selected element possible.

More particularly, the invention utilizes simultaneous testing to identify response contributions from individual matrix elements. A special binary sequence, or M-sequence, is utilized from which a viewed element can be identified through use of a response template or sample response obtained earlier from the user. The separability of the response contribution from the different matrix elements is guaranteed by the properties of M-sequence. See, for example, Solomon W. Golamb, *Shift Register Sequences*, 1982, Aegean Park Press, Laguna Hills, Calif.

The invention and objects and features thereof will be more readily apparent from the following detailed description and appended claims when taken with the drawing, in which:

Figure 1:
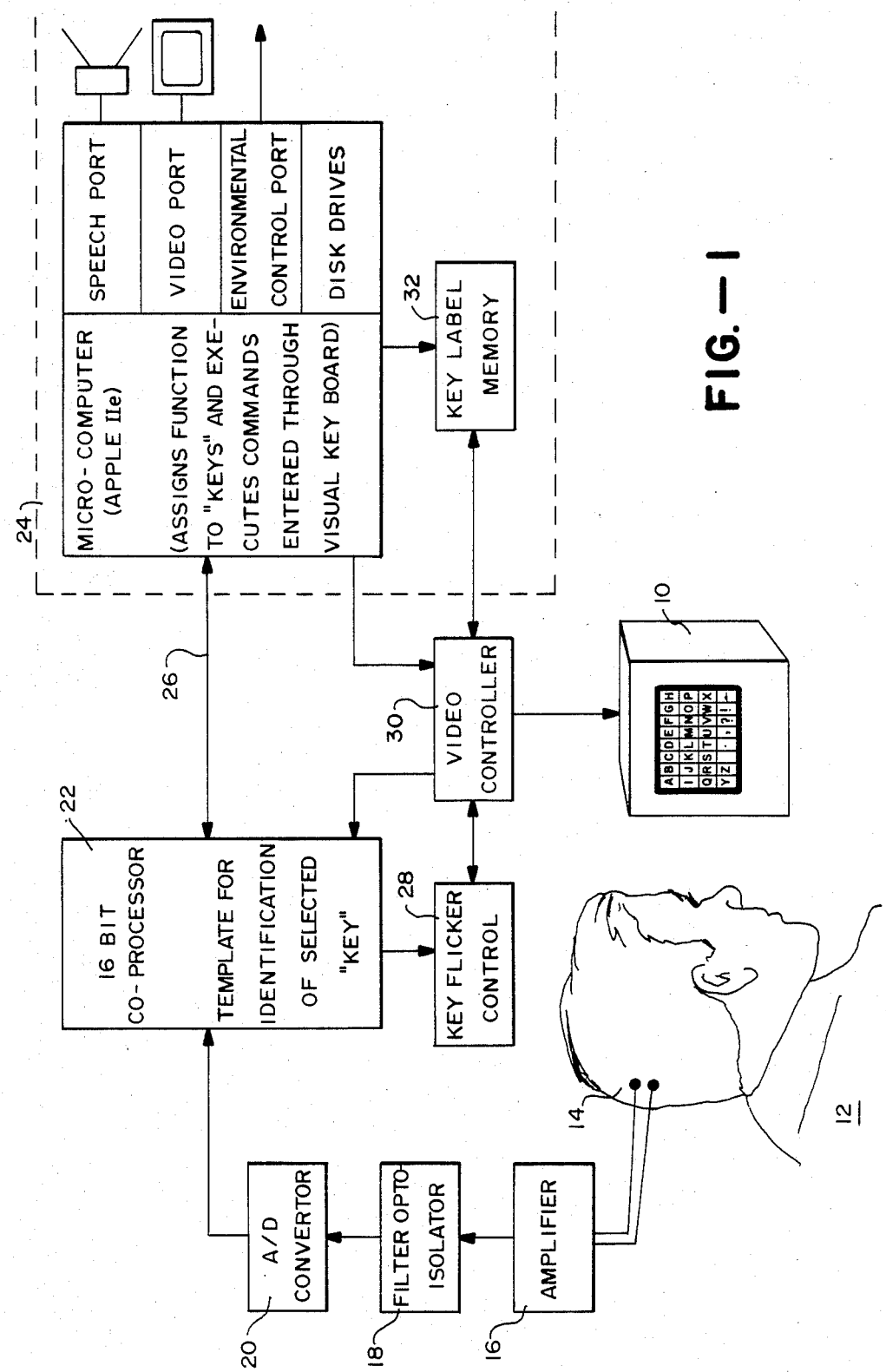
FIG. 1 is a functional block diagram of an oculo-encephalographic communication system in accordance with the invention.

Referring now to the drawings, FIG. 1 is a functional block diagram of an oculo-encephalographic communication system in accordance with the invention. A visual CRT display 10 having a plurality of independently controlled optical elements is provided for viewing by the viewer 12. In this embodiment the visual display comprises a video display and the independently controlled optical elements comprise a matrix of 32 elements which, for example, may correspond to alphabetical characters and special symbols. A pair of EEG electrodes 14 is pasted to the scalp of the viewer 12, and the EEG signal is amplified at 16, passes through an optical isolator 18, and then is converted from analog to digital form by converter 20. Each of the elements 14–20 are conventional in obtaining EEG signals.

The digital signals from converter 20 are applied to a processor 22 which identifies a unique code associated with each of the elements or keys of the matrix of display 10. After identification of a key or element, the key is transmitted to a computer 24 over bus 26 which responds to the identified key in accordance with an overlay for the matrix of display 10. Computer 24 then drives a speech port, a video port, a printer port, an environmental control port (e.g. switches), and peripheral memory devices.

In one embodiment the computer 24 comprised an Apple IIe microcomputer, and the computer 22 comprised a Saybrook, Inc. 16 bit co-processor commercially designed for operation with the Apple IIE computer.

The binary code associated with each element or key in the matrix of display 10 is provided by a key flicker control unit 28 operating under control of processor 22. Key flicker control 28 controls the binary codes associated with each of the matrix elements through video controller 30.

The overlay of functions associated with the matrix of display 10 is stored in a key label memory 32 under control of the processor 24 and can be exchanged during operation.

Figure 2:
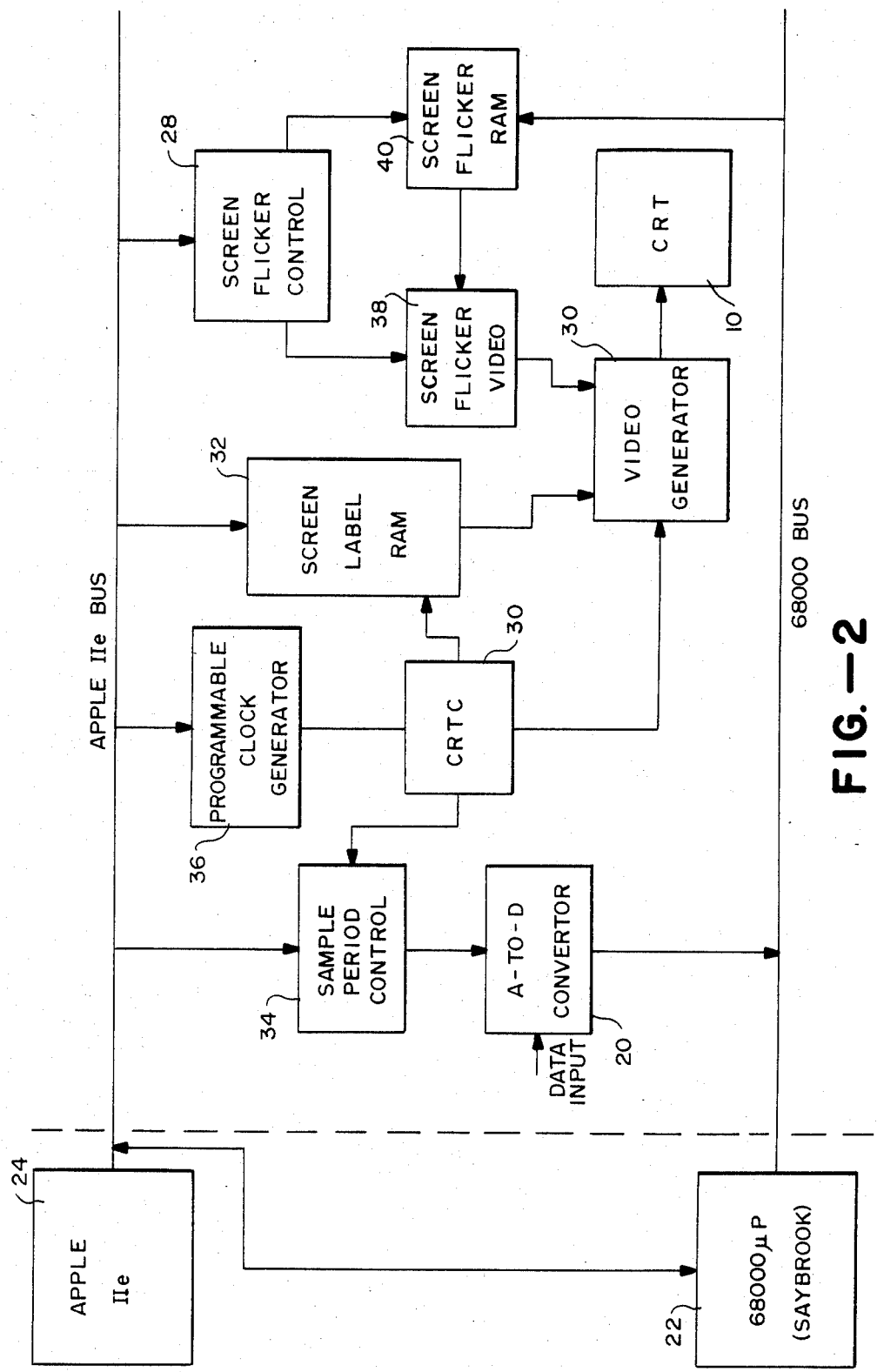
FIG. 2 is a functional diagram of the interface between the two computers of FIG. 1 and the CRT display.

FIG. 2 is a more detailed block diagram of the interface between processor 24, co-processor 22, and CRT display 10. The sample period for A/D converter 20 is established by the processor 24 and video controller through sample period control 34. Processor 24 also controls a programmable clock generator 36, the screen label RAM 32, and screen flicker control 28. Screen flicker control 28 controls the screen flicker video 38 and the screen flicker RAM 40. RAM 40 is connected to the bus of co-processor 22.

In operation, the user selects a character on the display simply by looking at it. Each flickering element contributes to the overall response which is derived from the viewer's scalp. In order to establish from the evoked potential measurements which one of the visual stimuli the person is viewing, it is necessary to isolate the individual response contributions. In principle, these contributions could be derived in a straightforward manner by sequential stimulation of the inputs and measurements of the corresponding response. However, such a sequential technique is very time consuming. For example, in the case of 31 inputs which are sequentially tested with flashes, the flashes have to be spaced at intervals of approximately 300 milliseconds in order to prevent overlap of the major response components in the EEG. A complete test of the entire input array would thus take 31×300 milliseconds or 9.3 seconds. Further, one sample of each response would be insufficient to provide an adequate response estimate. Assuming that 16 responses are necessary, a total time of 148.8 seconds or about 2.5 minutes would be required for an adequate test.

In accordance with the preferred embodiment of the invention, a technique of simultaneous testing is employed. Using the above example, 16 out of the 31 inputs are flashed at the 300 millisecond time intervals. Whether or not a particular input is flashed in the next time interval is determined by a special binary sequence or M-sequence. If the next element in the sequence is a 1, the input is flashed; if it is a 0, it is skipped. The sequence is the same for all inputs except for a relative delay of one step from one input to the next. M-sequences are always of length $2^{N-1}$ where "N" is an integer. In the present example the length is 31 and N must be 5.

Even though 16 inputs are always tested simultaneously, the contribution from each input can be perfectly isolated. This is due to a special property of M-sequences. It can be shown that if the response signal is multiplied by 1 in the time intervals following a flash on a specific element and by $-1$ when the element is skipped, and subsequently all time intervals are averaged together, the response contribution originating from that element is obtained. The responses from all the other inputs cancel out over the period of a full stimulation cycle. This method of isolating the response contributions from each of the individual channels is demonstrated in FIG. 5. For simplicity the case of 7 inputs is chosen for this illustration.

The efficiency of this technique can be further increased by reducing the temporal spacing between the transient stimuli. It can be shown that for linear systems the isolation of the input channels does not break down, even if the individual responses start to overlap. It is sufficient that an adequate relative delay of the m-sequence inputs from one channel to the next is maintained. To meet this requirement longer m-sequences (length 63, 127, ...) have to be used. It is desirable to increase the frame rate to the point where the visual system is maximally stimulated. Optimal efficiency is reached when the cross-power between the input sequence and the foveal response contribution is maximal. It is thus possible to "tune" the system to the human visual evoked response. Further, when the length of the m-sequence is increased to 63 or 127 with a corresponding increase of the relative delays between inputs to 2 or 4, it becomes possible to resolve 32 instead of 31 inputs.

In some individuals the evoked response to a flash has the peculiarity that it changes polarity depending on whether the flash is presented in the upper or lower half of the visual field. In such cases every stimulus element is divided into an upper and lower half. By counter-modulating the two halves (one half is flashed whenever the other one is skipped) their contributions to the foveal response will add rather than cancel in the above averaging procedure.

Once the response contributions of the individual stimulus fields have been isolated, they have to be measured and the largest one has to be determined. A suitable measure is given by the square root of their power:

$$\int_o^T R_i^2(t)dt;$$

$r_i(t)$ response of input i.

It can be shown, however, that the effect of noise contamination can be reduced if, instead of squaring the responses $R_i$, we multiply them with an appropriate response template:

$$\int_o^T R_i(t)T_i(t)dt.$$

The template $T_i$ is the foveal response for input i. Since all templates are identical up to a relative delay, only one has to be recorded. In a separate recording session the subject fixates one particular field on the display with all the other fields masked off. For good signal-to-noise ratio, 10 to 20 minutes worth of data are accumulated in small segments. Once a template has been obtained for a particular person it can be used indefinitely, as long as the electrode placement is not changed.

The use of a template brings an additional advantage. It permits doubling the number of selectable stimulus elements without resorting to a longer input cycle.

Thus a second set of 32 fields is added which is modulated with the inverted input sequences of the first set. When the response contributions are extracted as described above, they are also inverted with respect to the first set. Unlike the computation of the power, the multiplication with the template preserves this minus sign and thus makes the second set discriminable from the first one.

It is clear from the above considerations that the response to an entire stimulus cycle is required for accurate isolation of the response contributions. Such a response cycle is stored in a rotating buffer. With accumulation of every new data point, the last sample in the buffer is dropped. All the scalar products between responses and template vectors are updated and the largest one is selected. Before an output of the corresponding keyboard character is generated, three conditions have to be satisfied:

1. A response contribution has to be larger than all the others.
2. It also has to be larger than a given threshold value.
3. It has to be maximal for a given length of time.

The threshold criterion is designed to prevent false responses. The threshold is proportional to the square root of the total power of the EEG data contained in the rotating buffer. It is updated with the accumulation of every new data point. When the user generates more muscle artifacts by head movements or chewing, the overall signal increases, but not the actual response power. The threshold will thus be pushed up and out of range so that no false crossings can occur. This criterion makes the system self-calibrating.

The time criterion also helps to eliminate spurious responses of the system. It acts as a low-pass filter reducing the susceptibility to fast fluctuations.

The response rate is determined largely by the length of the stimulus cycle. Whenever the user shifts his or her gaze to a new stimulus element, it takes time for the rotating buffer to be filled with the corresponding data. A response will generally occur after about ⅔ of the buffer has been updated. With a longer stimulus cycle the response of the system becomes slower but more reliable, since the estimate is based on more data. At present, the best performance is reached with a cycle length of about 2.5 seconds.

Attached hereto and incorporated by reference are the program listings for the template recording program including sub-routines for control of the Apple HRG screen, cross-correlation of sample with the M-sequence, and template transfer. Also attached and incorporated by reference are detailed schematics of the processor and co-processor interface elements.

The technique described above can be refined in many ways:
1. Instead of extracting the responses originating from the different input channels and comparing their power, overall response is multiplied (in the sense of a scalar product) with foveal response templates with relative delays corresponding to the different input channels. This results in improvement of the signal to noise ratio, since the template can be obtained by averaging over extended. Unlike the power, this 'scaler product' can be positive or negative. It is thus possible to distinguish the responses from two inputs modulated with relatively inverted signals. The number of resolvable input channels can thus be doubled without a sacrifice in response speed.
2. The time between flashes can be increased beyond the point where the responses to consecutive flashes start to overlap. In this way more response power can be generated. In order to prevent cross-talk between the input channels it is important, however, that the length of the m-sequence be increased by a factor of two or four and the relative delay from one input to the next be increased to two or four steps, respectively.

A further improvement in performance can be achieved if the temporal modulation of the inputs is not in terms of flash or no flash, but rather in terms of a flash in phase with the fundamental component of the previous flash or a flash 180 degrees out of phase. From this the low frequency components of the flicker sequence are greatly reduced making the flicker of the stimuli less perceptible and more acceptable to the user. Also, the response power originating from individual inputs is more evenly distributed over the duration of an entire stimulus loop. This makes it possible to identify the fixated target element long before completion of a cycle simply on the basis of growth in response energy. The theoretical lower limit for the response data necessary for the target identification for $2^{**}n$ targets is n base intervals (n flashes).

While the present system works with two electrodes, performance could be improved by using more electrodes. Further, telementry can be used to transmit the signal to the computer. This gives the user unrestricted freedom of motion. Additionally, electrodes can be implanted on the dura outside the brain. The signal can be amplified and transmitted through the skin by a miniature implanted circuit. In this way artifacts from muscles in the neck and scalp region are virtually eliminated and the signal to noise ratio is increased. A great improvement of the performance of the system can be expected and the need to attach EEG electrodes to the scalp is eliminated. Since the device would be powered through the skin by induction, no penetration of electrical leads through the skin is required and safe and reliable performance over many years can be expected.

Thus, while the invention has been described with respect to a specific embodiment, the description is illustrative of the invention and is not to be construed as limiting the invention. Various modifications and applications may occur to those skilled in the art without departing from the true scope and spirit of the invention as defined by the appended claims.

What is claimed is:

1. A method of oculo-encephalographic communication comprising the steps of
    providing a plurality of visual stimuli and a unique code signal corresponding to each of said visual stimuli,
    obtaining an EEG signal of a viewer while viewing said visual stimuli,
    adaptively identifying one of said unique code signals with corresponding ones of said EEG signals, and adaptively identifying one of said visual stimuli viewed by said viewer from each identified code signal.

2. The method as defined by claim 1 wherein said code comprises an M-sequence binary code.

3. An oculo-encephalographic communication system comprising
    a visual display for projecting a plurality of independently controlled visual stimuli,
    means for controlling said plurality of visual stimuli whereby each stimulus transmits a unique code signal,
    means for obtaining an EEG signal from a viewer while viewing said display, and
    means for adaptively identifying a unique code with a corresponding one of said EEG signals thereby identifying one of said visual stimuli viewed by said viewer.

4. The system as defined by claim 3 wherein said visual display comprises a video display having a matrix of elements for viewing.

5. The system as defined by claim 4 wherein said unique code is an M-sequence binary code.

6. The system as defined by claim 5 wherein said means for identifying an optical element assigns a $+1$ value to a stimulated response, a $-1$ value to lack of a stimulated response, and sums all values.

7. The system as defined by claim 3 and further including means responsive to identification of an optical element.

8. The system as defined by claim 7 wherein said means responsive to identification of an optical element includes computer means for controlling an overlay for said optical matrix.

* * * * *